United States Patent
Toth et al.

[11] Patent Number: 5,982,846
[45] Date of Patent: Nov. 9, 1999

[54] METHODS AND APPARATUS FOR DOSE REDUCTION IN A COMPUTED TOMOGRAPH

[75] Inventors: Thomas L. Toth, Brookfield; Neil B. Bromberg, Milwaukee, both of Wis.

[73] Assignee: General Electric Company, Milwaukee, Wis.

[21] Appl. No.: 09/059,469

[22] Filed: Apr. 13, 1998

[51] Int. Cl.[6] .................................................. A61B 6/03
[52] U.S. Cl. ............................................. 378/19; 378/901
[58] Field of Search ................... 378/4, 19, 901

[56] References Cited

U.S. PATENT DOCUMENTS

| 5,430,784 | 7/1995 | Ribner et al. | 378/19 |
| 5,867,555 | 2/1999 | Popescu et al. | 378/16 |

*Primary Examiner*—David Vernon Bruce
*Attorney, Agent, or Firm*—John S. Beulick; Christian G. Cabou; Phyllis Y. Price

[57] ABSTRACT

Methods and apparatus for dose reduction in a computed tomography (CT) system are described. In one embodiment, the CT system includes a configurable multislice detector array and an adjustable source collimator. The detector array includes a photodiode cell array optically coupled to a scintillator array. The photodiode array includes a plurality of photodiodes arranged in rows and columns that may be combined to collect slice data from a number of inner and outer slices. The CT system also includes an x-ray source and a collimator. The x-ray source generates an x-ray beam that is collimated by the collimator to define the thickness of each outer slice. In operation, an operator determines the quantity and thickness of inner slices and the thickness of each outer slice. After altering the detector and collimator configuration, as defined by an operator, slice data for each inner slice and each outer slice is gathered.

18 Claims, 4 Drawing Sheets

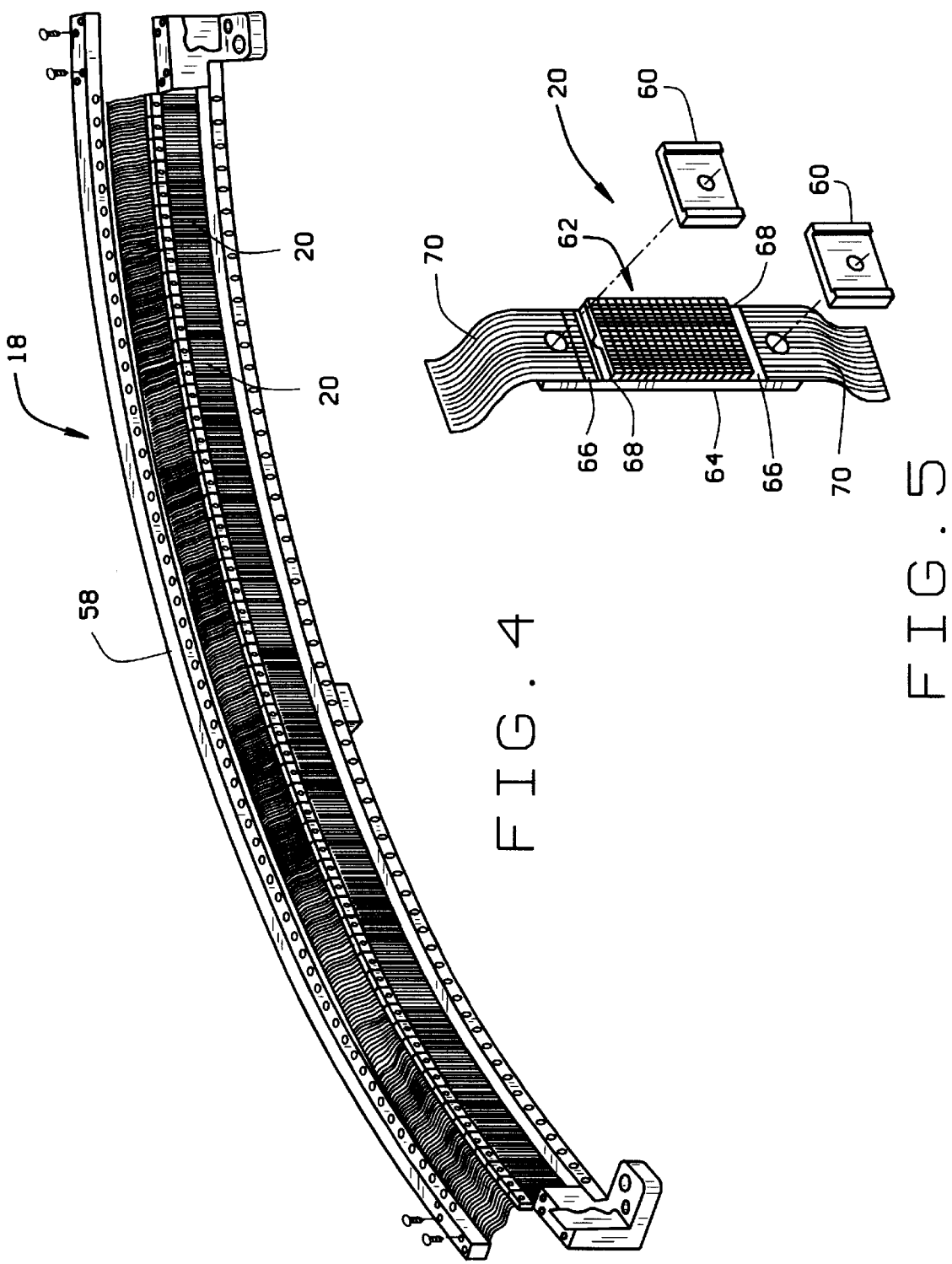

METHODS AND APPARATUS FOR DOSE REDUCTION IN A COMPUTED TOMOGRAPH

FIELD OF THE INVENTION

This invention relates generally to computed tomograph (CT) imaging and, more particularly, to reducing x-ray exposure and improving x-ray efficiency in a multislice CT system.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

A multislice CT system requires source collimation to flood the detector with a uniform x-ray beam intensity in the z-axis. This is necessary to avoid image artifacts that would otherwise be caused by the normal movement of a non-uniform x-ray beam over a non-uniform z-axis detector response. Unfortunately, much of the x-ray beam typically falls unused off the ends of the detector resulting in low dose efficiency and a high patient dose.

Accordingly, it would be desirable to provide a CT system that utilizes all of the x-ray beam which allows selection of the number and thickness of the scan slices to reduce patient x-ray dosage and improve x-ray beam efficiency.

SUMMARY OF THE INVENTION

These and other objects may be attained by a CT system which, in one embodiment, utilizes a configurable multislice detector array and a source collimator to improve x-ray beam efficiency and reduce patient x-ray dosage. The CT system multislice detector includes a plurality of detector modules. Each detector module has a photodiode cell array optically coupled to a scintillator array. The photodiode array includes a plurality of photodiodes arranged in rows and columns. A post patient collimator array is aligned and positioned adjacent to the scintillator array to collimate the x-ray beams after passing through a patient. Each detector module further includes a switch apparatus and a decoder. The switch apparatus is electrically coupled between the photodiode output lines and a CT system data acquisition system (DAS). The switch apparatus, in one embodiment, is an array of FETs and alters the number of slices and the thickness of each slice by allowing each photodiode output line to be enabled, disabled, or combined with other photodiode output lines. The slices may be configured as inner slices and outer slices. The CT system also includes an x-ray source that generates an x-ray beam. The x-ray beam is collimated by the source collimator to define the thickness of the outer slices.

In operation, an operator determines the quantity and thickness of inner slices and the thickness of each outer slice. The appropriate photodiode outputs of the detector array are then electrically combined to form the selected number of inner slices with each having the selected thickness. The source collimator is then adjusted so that the outer slices have the selected thickness. Slice data for each inner slice and each outer slice are then gathered from the detector array.

By using the above described CT system the number and thickness of scan slices is selectable. Such CT system provides reduced patient x-ray dosage and improved x-ray beam efficiency.

BRIEF DESCRIPTION OF THE DRAWINGS

FIG. 4 is a perspective view of a CT system detector array.

FIG. 5 is a perspective view of a detector module.

DETAILED DESCRIPTION

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular source collimator are described, other detectors or collimators could be used in connection with the system, and the present invention is not limited to practice with any one particular type of detector. Specifically, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis joined together in either direction to acquire multislice scan data simultaneously, can be utilized. Similarly, although the source collimator described below includes two cams for adjusting the z-axis width of the x-ray beam, other known source collimators may be utilized. Generally, the system is operable in a multislice mode to collect 1 or more slices of data. Axial and helical scans can be performed with the system, and cross section images of a scanned object can be processed, reconstructed, displayed and/or archived.

Figure 1:
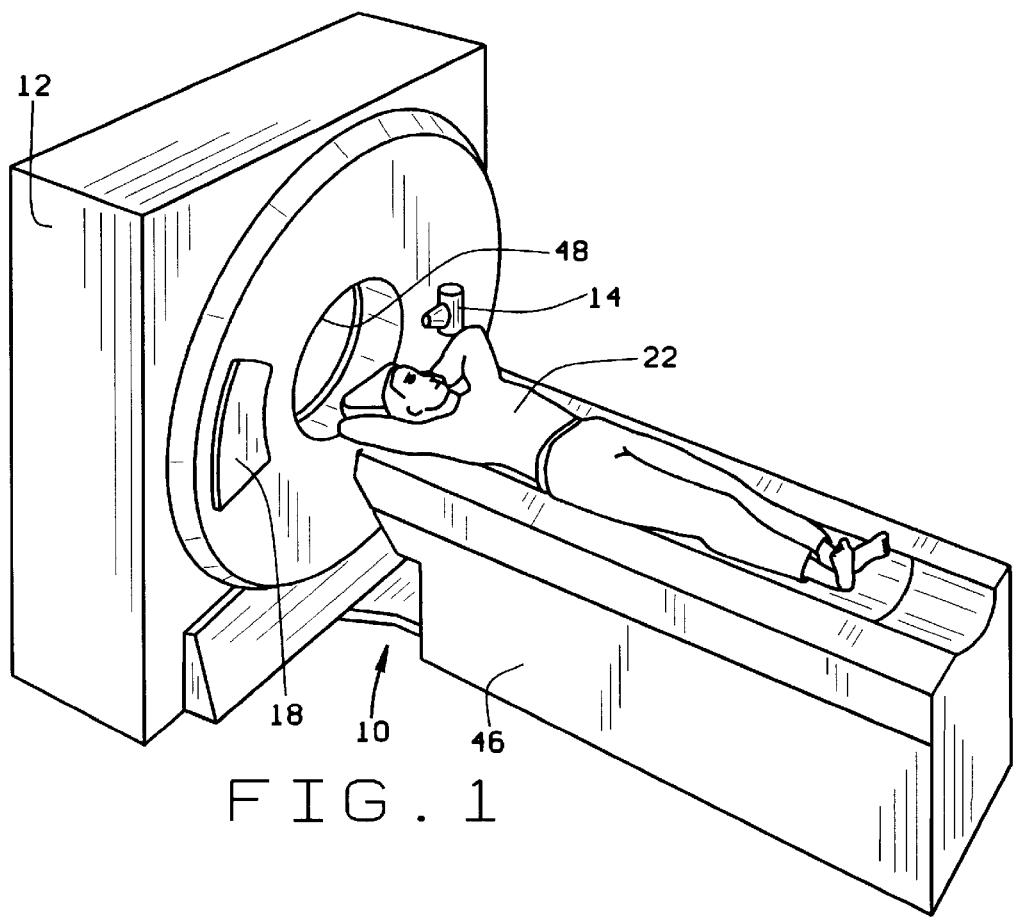
FIG. 1 is a pictorial view of a CT imaging system.
Figure 2:
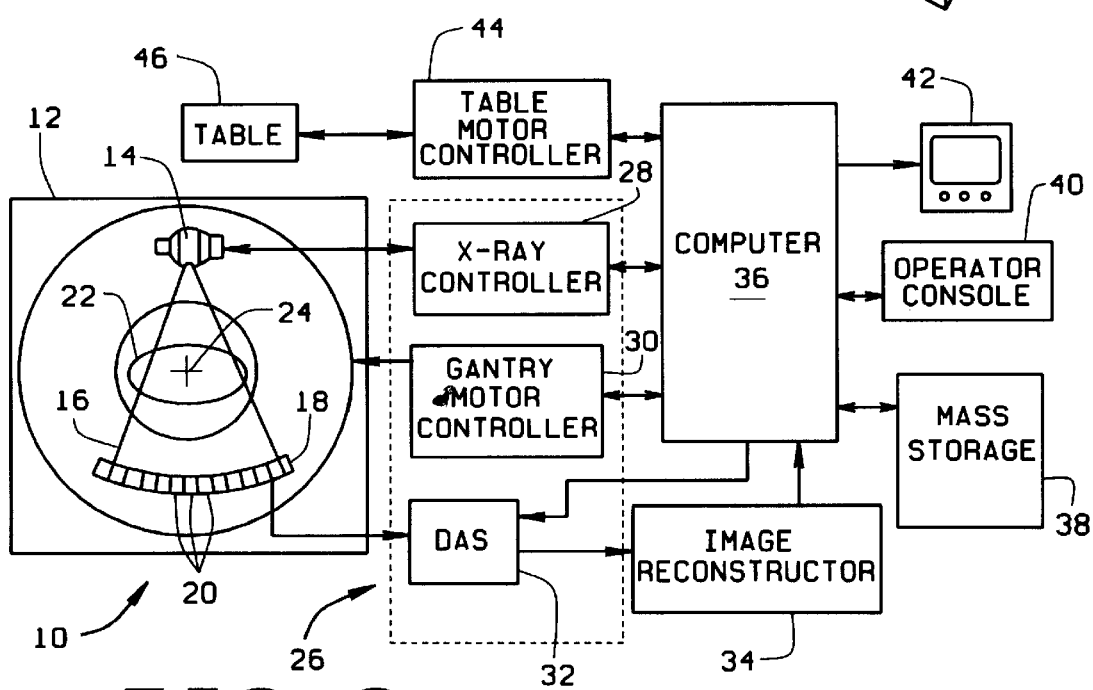
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 also operates a table motor controller 44 which controls a motorized table 46 to position patient 22 in gantry 12. Particularly, table 46 moves portions of patient 22 through a gantry opening 48.

Figure 3:
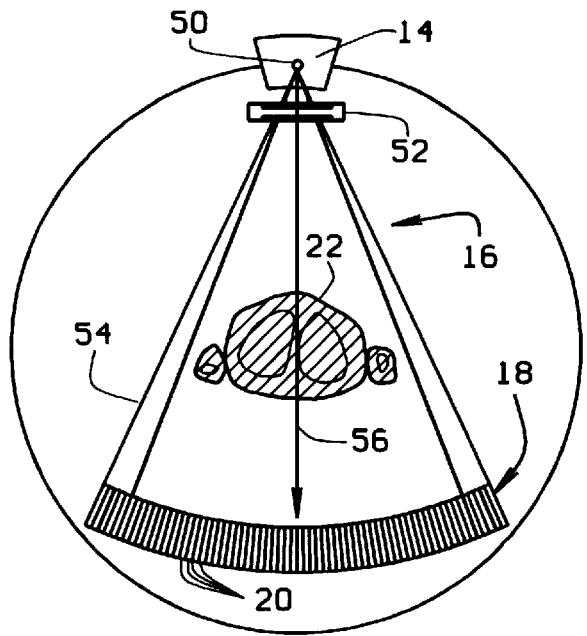
FIG. 3 is a schematic view of the CT imaging system with a collimator.

Referring to FIG. 3, and with respect to operation of x-ray source 14, x-ray beam 16 emanates from a focal spot 50 of source 14. X-ray beam 16 is collimated by collimator 52, and a collimated beam 54 is projected toward detector array 18 along a fan beam axis 56 centered within beam 16.

The architecture of system 10 described above provides many important advantages, including that detector array 18 and collimator 52 can be configured so that system 10 reduces x-ray dosage to patient 22 and improves x-ray beam efficiency. Particularly, by configuring detector array 18 and adjusting collimator 52, CT system 10 has a selectable number of inner slices with each slice having a selectable slice thickness and a selectable number of outer slices having a selectable slice thickness. Further details regarding detector array 18 and collimator 52 are set forth below.

As shown in FIGS. 4 and 5, detector array 18 includes a plurality of detector modules 20. Each detector module 20 is secured to a detector housing 58 by plates 60. Each module 20 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 20 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of photodiode array 52 are electrically connected to DAS 32, resulting in 16 separate, simultaneous slices of data being sent to DAS 32. Of course, many other slice combinations are possible. Further details regarding detector module 20 are set forth in co-pending U.S. patent application Ser. No. (15-CT-4631), Photodiode Array For A Scalable Multislice Scanning Computed Tomography System, which is assigned to the present assignee and hereby incorporated herein, in its entirety, by reference.

In one specific embodiment, detector 18 includes fifty-seven detector modules 20. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, having two inner slices and two outer slices, so that data is collected for four slices from one or more rows of the photodiode array. Depending upon the specific configuration of the FETs as defined by decoder control lines, various combinations of outputs of the photodiode array can be enabled, disabled, or combined so that the inner slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
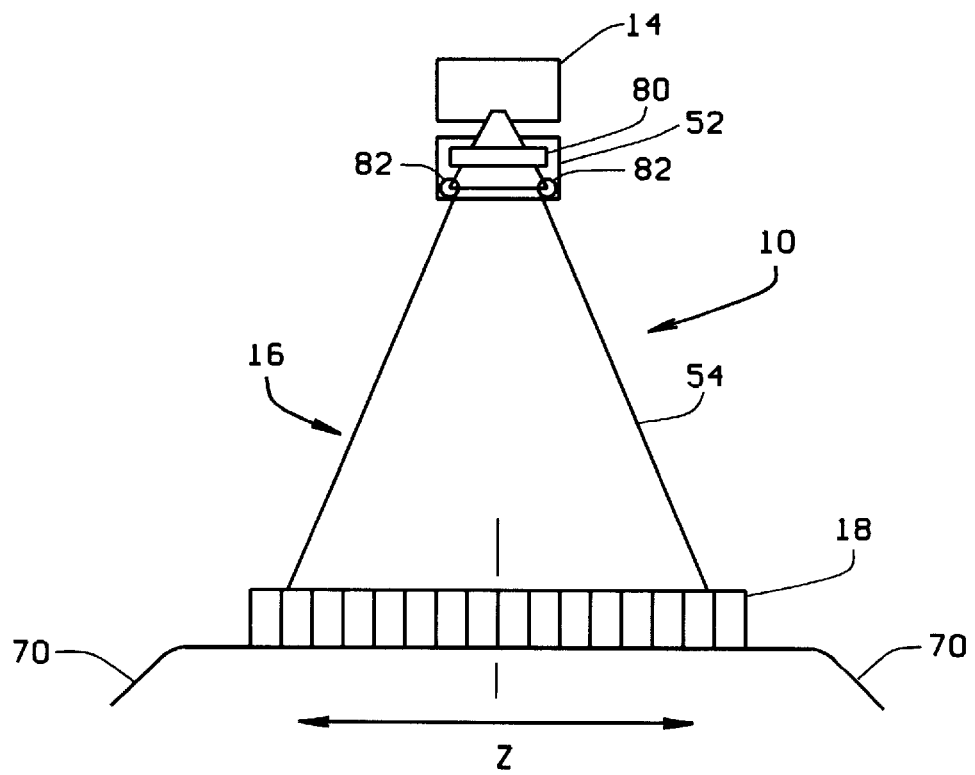
FIG. 6 is a schematic illustration of x-ray generation and detector components viewed from a side of the gantry.

Referring to FIG. 6, and in multislice scanning, data is collected at various z-axis locations. Particularly, FIG. 6 is a schematic illustration of system 10 viewed from a side of the gantry 12. In one embodiment, collimator 52 includes a bowtie filter 80 and tungsten cams 82. The position of cams 82 is controlled by x-ray controller 28 which receives its commands from computer 36. Stepper motors (not shown), for example are connected to cams 82 for precisely controlling the position of cams 82. Cams 82 of collimator 52 can be independently adjusted with respect to the spacing between cams 82 and their location relative to the center of the collimator opening depending on the user selected data collection mode.

The following description relates to operation of cam collimator 52 and detector 18 for providing a selectable number of slices and slice resolution, or thickness. Although the operation of cam collimator 52 and the operation of detector array 18 are sometimes described separately herein, it should be understood that collimator 52 and detector 18 operate in combination to provide the desired number of slices and slice thickness.

In operation, the operator determines an appropriate thickness and quantity of slices as required by the scan procedure to be performed. Detector array 18 and collimator 52 are then configured for the desired slice thickness and quantity. The configuration of detector array 18 and collimator 52 minimize the x-ray dosage to patient 22 and improve the efficiency of x-ray beam 16 by fully utilizing the z-axis of x-ray beam 16. Specifically, in FIG. 7, detector 18 is divided into a number of inner slices 100 and a number of outer slices 102. The thickness of each inner slice 100 is determined by the number of photodiode array outputs that are combined using switch apparatus 66 as defined by the operator. The thickness of outer slice 102 is determined by collimator 52, by adjusting the position of collimator cams 82 in the z-axis direction.

Figure 7A:
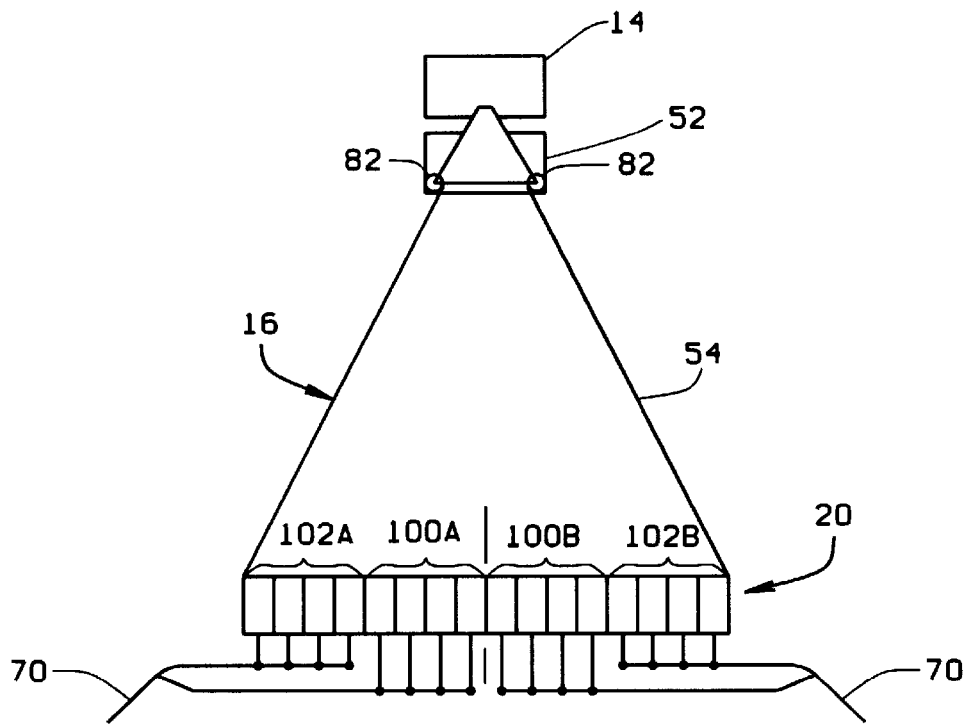
FIGS. 7a and 7b schematically illustrate collection of scan data for various numbers of slices and slice thickness.

For example, if the operator selects two inner slices of 5.0 mm and two outer slices of 5.0 mm, system 10 may be configured as shown in FIG. 7a. Particularly, the outputs of the photodiode array are combined, using switch apparatus 66, to form inner slices 100A and 100B, each having a slice thickness of 5.0 mm where each row of detector module 20 is 1.25 mm wide. Specifically, four outputs of the photodiode array are electrically coupled by switch apparatus 66 to form inner slice 100A. Slice 100B is also formed by combining four outputs of the photodiode array.

Source collimator cams 82 are separated in the z-axis direction to provide 20.0 mm of source collimation. Outer slices 102A and 102B each have a slice thickness of 5.0 mm as determined by ((total slice thickness—total inner slice thickness)/number of outer slices), or as shown in FIG. 7a, (((16 slices×1.25 mm/row) - (inner slice 102A thickness of 5.0 mm+inner slice 102B thickness of 5.0 mm))/2 outer slices)=5.0 mm per outer slice. The photodiode array outputs are combined using switch apparatus 66 to gather data for outer slices 102A and 102B. Specifically, four respective outputs of the photodiode array are electrically combined by switch apparatus 66 to form respective outer slices 102A and 102B. Slice data from inner slices 100A and 100B and outer slices 102A and 102B are supplied to DAS 32 via cable 70.

Figure 7B:
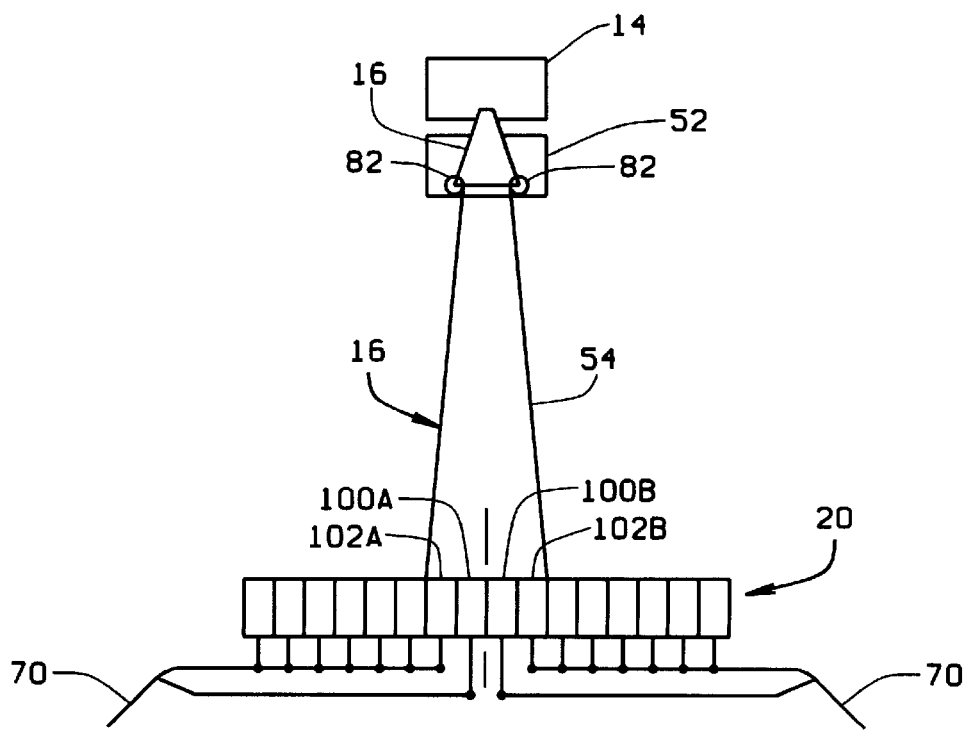

For four slices of data with a 1.25 mm slice thickness, the detector configuration shown in FIG. 7b may be utilized. Particularly, the photodiode array outputs form two inner slices 100A and 100B, each having a thickness of 1.25 mm. Cams 82 are not separated as wide apart as for the 5.0 mm slice thickness (FIG. 7a). Rather, cams 82 are moved closer together in the z-axis direction to provide 5.0 mm collimation, defining outer slices 102A and 102B each having a thickness of 1.25 mm. Although outer slices 102A and 102B are defined by collimator 52 to have a thickness of 1.25 mm each, the remaining outputs of photodiode array 52 are combined for outer slices 102A and 102B using switch apparatus 66. Particularly, seven outputs of the photodiode array are combined by switch apparatus 66 to gather data for outer slice 102A. Similarly, seven outputs of the photodiode array are combined to gather data for outer slice 102B. Referring now to inner slices 100A and 100B, data is gathered from one output of the photodiode array for inner slice 100A and from one output of the photodiode array for inner slice 100B. Data from inner slices 100A and 100B and outer slices 102A and 102B are supplied to DAS 32 via flex cables 70.

Of course, many other combinations of inner slice thickness and quantity and outer slice thickness are possible using system 10. For example, if detector module 20 includes an N×M cell array, the maximum number of inner slices is N, where the number of outer slices is zero. Additionally, if both ends, or outer portions, of detector module 20 are defined as outer slices, the number of inner slices ranges between 1 and N−2 inner slices.

The above described CT system enables selection of the number and thickness of inner slices and outer slice thickness to reduce patient x-ray dosage improve x-ray beam efficiency.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

We claim:

1. A method for reducing x-ray dose exposure in a multi-slice computed tomography system, the computed tomography system including an x-ray source for producing an x-ray beam along an imaging plane, a source collimator for collimating the x-ray beam, and at least one multislice detector module including a plurality of detector cells extending in a z-axis, said method comprising the step of:

configuring the detector module to have a selected number of slices, at least one inner slice thickness selected based on a number of detector cells combined and at least two outer slices each having a thickness based on the source collimator setting.

2. A method in accordance with claim 1 wherein the source collimator setting is selected by positioning the source collimator.

3. A method in accordance with claim 1 wherein each detector module includes an array of cells, and wherein the step of configuring the detector module to have a selected number of slices comprises the step of combining a number of cell data signals for each selected inner slice thickness.

4. A method in accordance with claim 3 wherein the step of configuring the detector module to have a selected number of slices further comprises the step of combining a number of cell data signals for each selected outer slice thickness.

5. A method in accordance with claim 4 wherein each detector module further includes a switch apparatus electrically coupled to the cell array, wherein the step of combining a number of cell data signals comprises the step of configuring the switch apparatus to combine a number of cell data signals for each inner slice.

6. A method in accordance with claim 5 wherein the step of combining a number of cell data signals further comprises the step of configuring the switch apparatus to combine a number of cell data signals for each outer slice.

7. A method in accordance with claim 4 wherein the computed tomography system includes a data acquisition system, and wherein the step of combining a number of cell data signals for each selected inner slice thickness comprises the step of configuring the data acquisition system to combine a number of slice cell data signals to provide the selected slice thickness for each inner slice.

8. A method in accordance with claim 7 wherein combining a number of cell data signals further comprises the step of configuring the data acquisition system to combine a number of cell data signals to provide the desired slice thickness for each outer slice.

9. A method in accordance with claim 1 wherein the step of configuring the detector module to have a selected number of slices comprises the step of selecting at least two inner slices.

10. A method in accordance with claim 1 wherein each detector module includes a N×M cell array, where N is the maximum number of slices, and wherein the step of configuring the detector module to have a selected number of slices comprises the step of selecting between 1 and N−2 inner slices.

11. A method in accordance with claim 10 wherein the step of selecting between 1 and N−2 inner slices defines two outer slices located on opposite sides of the selected inner slices.

12. A system for reducing x-ray dose exposure in a computed tomography system, the computed tomography system including an x-ray source, a source collimator, and at least one multislice detector module, each detector module including a plurality of detector cells extending in a z-axis, said system configured to:

combine a number of detector cells to form at least one inner slice; and position the source collimator to define a thickness for a number of outer slices.

13. A system in accordance with claim 12 wherein the computed tomography system further comprises a computer coupled to the source collimator and to the detector module for enabling an operator to select the inner slice thickness and number of inner slices.

14. A system in accordance with claim 12 wherein said number of inner slices comprises at least one slice.

15. A system in accordance with claim 12 wherein said number of inner slices comprises two slices.

16. A system in accordance with claim 12 wherein said number of inner slices comprises more than two slices.

17. A system in accordance with claim 12 wherein the source collimator comprises a cam collimator comprising at least one adjustable cam.

18. A system in accordance with claim 12 wherein said system comprises a plurality of detector modules.

* * * * *